US008978649B2

(12) United States Patent
Chalvignac

(10) Patent No.: US 8,978,649 B2
(45) Date of Patent: Mar. 17, 2015

(54) BREATHING ASSISTANCE DEVICE WITH SEVERAL SECURE RESPIRATOR MODES AND ASSOCIATED METHOD

(71) Applicant: ResMed Paris SAS, Paris (FR)

(72) Inventor: Philippe Auguste Chalvignac, Moissy Cramayel (FR)

(73) Assignee: ResMed Paris SAS (FR)

( * ) Notice: Subject to any disclaimer, the term of this patent is extended or adjusted under 35 U.S.C. 154(b) by 0 days.

(21) Appl. No.: 13/739,327

(22) Filed: Jan. 11, 2013

(65) Prior Publication Data

US 2013/0125890 A1   May 23, 2013

Related U.S. Application Data

(63) Continuation of application No. 13/014,202, filed on Jan. 26, 2011, now Pat. No. 8,381,725, which is a continuation of application No. 10/544,318, filed as application No. PCT/IB03/04044 on Aug. 28, 2003, now Pat. No. 7,891,353.

(60) Provisional application No. 60/498,537, filed on Aug. 28, 2003.

(30) Foreign Application Priority Data

Aug. 29, 2002   (FR) ..................................... 02 10716

(51) Int. Cl.
*A61M 16/00*   (2006.01)
*A61M 16/20*   (2006.01)

(52) U.S. Cl.
CPC ....... *A61M 16/0057* (2013.01); *A61M 16/0051* (2013.01); *A61M 16/0066* (2013.01);
(Continued)

(58) Field of Classification Search
CPC ............ A61M 16/00; A61M 16/0051; A61M 16/0057; A61M 16/0066; A61M 16/0072; A61M 16/06; A61M 16/08; A61M 16/0808; A61M 16/0816; A61M 16/0875; A61M 2016/00; A61M 2016/0003; A61M 2016/0015; A61M 2016/0018; A61M 2016/0021; A61M 2016/0024; A61M 2016/0057; A61M 2016/0063; A61M 2016/0066; A61M 2016/0069; A61M 2016/06; A61M 2016/08; A61M 2016/0816; A61M 2016/0039; A61M 2205/3584; A61M 16/12; A61M 16/20; A61M 16/208; A61M 16/0042; A61M 2205/18; A61M 2205/3592; A61M 2205/3523; Y10S 128/903; Y10S 128/904; A61B 5/0002; A63B 2225/50
USPC ............. 128/200.24, 204.26, 204.21, 202.22, 128/205.23, 204.18–205.12
See application file for complete search history.

(56) References Cited

U.S. PATENT DOCUMENTS 3,595,228 A   7/1971   Simon et al.
3,949,749 A   4/1976   Stewart
(Continued)

FOREIGN PATENT DOCUMENTS

WO   9611717 A1   4/1996
WO   9706844 A1   2/1997
WO   0051663 A2   9/2000

*Primary Examiner* — Annette Dixon
(74) *Attorney, Agent, or Firm* — Lerner, David, Littenberg, Krumholz & Mentlik, LLP

(57) ABSTRACT

A breathing assistance device, capable of operating according to several respiratory modes forming a list of possible modes. The device is equipped with a mechanism for selecting a desired mode from a group of modes that can be selected. The device also includes a mechanism for realizing a configuration diagnostic of the device, a mechanism for associating with authorization level with each possible mode, according to the results of the diagnostic, with the lowest authorization level corresponding to unauthorized modes, a mechanism for authorizing only the selection of authorized modes, in such a way that selecting unauthorized modes is impossible.

23 Claims, 2 Drawing Sheets

(52) U.S. Cl.
CPC ........... *A61M16/20* (2013.01); *A61M 16/0069* (2013.01); *A61M 16/205* (2013.01); *A61M 2016/0021* (2013.01); *A61M 2016/0039* (2013.01); *A61M 2205/702* (2013.01)
USPC ............. 128/204.21; 128/204.18; 128/200.24

(56) References Cited

U.S. PATENT DOCUMENTS

| | | | |
|---|---|---|---|
| 4,155,357 A | 5/1979 | Dahl | |
| 4,287,886 A | 9/1981 | Thompson | |
| 4,550,726 A | 11/1985 | McEwen | |
| 5,551,419 A * | 9/1996 | Froehlich et al. | 128/204.23 |
| 5,626,129 A | 5/1997 | Klimm et al. | |
| 5,881,717 A | 3/1999 | Isaza | |
| 6,024,089 A | 2/2000 | Wallace et al. | |
| 6,158,430 A | 12/2000 | Pfeiffer et al. | |
| 6,269,810 B1 | 8/2001 | Brooker et al. | |
| 6,349,724 B1 * | 2/2002 | Burton et al. | 128/204.18 |
| 6,578,575 B1 | 6/2003 | Jonson | |
| 6,591,834 B1 | 7/2003 | Colla et al. | |
| 6,668,824 B1 | 12/2003 | Isaza et al. | |
| 6,679,432 B1 | 1/2004 | Arnold | |
| 7,905,231 B2 * | 3/2011 | Chalvignac | 128/204.21 |
| 2002/0017296 A1 | 2/2002 | Hickle | |
| 2002/0088465 A1 | 7/2002 | Hill | |
| 2002/0185127 A1 | 12/2002 | Melker et al. | |
| 2002/0185130 A1 | 12/2002 | Wright et al. | |
| 2008/0264417 A1 | 10/2008 | Manigel et al. | |

* cited by examiner

BREATHING ASSISTANCE DEVICE WITH SEVERAL SECURE RESPIRATOR MODES AND ASSOCIATED METHOD

CROSS-REFERENCE TO RELATED APPLICATIONS

This application is a continuation of U.S. application Ser. No. 13/014,202, filed Jan. 26, 2011 which is a continuation of U.S. application Ser. No. 10/544,318, filed on Jun. 22, 2006, now U.S. Pat. No. 7,891,353, which is a national phase entry under 35 U.S.C. §371 of International Application No. PCT/IB2003/004044, filed Aug. 28, 2003 which claims the benefit of U.S. Provisional Application No. 60/498,537, filed Aug. 28, 2003, and France Application Serial No. 0210716, filed Aug. 29, 2002, the disclosures of which are hereby incorporated herein by reference.

FIELD OF THE TECHNOLOGY

This invention relates to breathing assistance devices.

More precisely, the invention relates to a breathing assistance device, capable of operating according to several respiratory modes forming a list of possible modes, and equipped with means of selecting a desired mode from a group of modes that can be selected.

And the invention also relates to a method of implementing such a device.

BACKGROUND OF THE TECHNOLOGY

Devices of the type mentioned above already exist.

Note that generally speaking, breathing assistance devices are designed to provide a patient with respiratory assistance, using a source of gas (oxygenated mixture) which can be connected to a turbine.

These devices can be sorted into two main categories:

(a) Ventilators. These devices are of the barometric type and realize ventilation through leakage (via vents on the mask located on the patient side), (b) Respirators. These devices include an expiratory valve to realize ventilation without leakage. They include a "simple" circuit (a single duct between the patient and the device), or double.

Ventilators operate with a single duct between the device and the patient. This single duct finishes on the patient side with a vented mask, allowing leakage.

Ventilators generally operate in a mode of the "barometric" type according to which the inspiratory and expiratory phases are mainly triggered by pressure measurements.

Note that in general, certain breathing assistance devices can operate in a mode of the volumetric type (in which the devices forces a given quantity of air into the duct).

The operating modes will be discussed further in this text.

Ventilators are of the CPAP type or of the BPAP type.

The CPAP type (acronym for the Anglo-Saxon denomination Continuous Positive Airway Pressure—this type can also be designated by the acronym PPC, for Pression Positive Continue) designates ventilators with a single pressure level.

In these ventilators, turbine speed is regulated by a pressure measurement in the single duct.

The single pressure setting is generally set to a value less than 20 mbars (this value is expressed as excess pressure in relation to atmospheric pressure), which limits the use of such ventilators to treating superficial pathologies.

Ventilators of the BPAP type (acronym for the Anglo-Saxon denomination Bilevel Positive Airway Pressure, this acronym is a registered trademark—and this type can also be designated by the acronym VNDP for Ventilation Nasale a Deux niveaux de Pression) using the same general architecture, but operating with two pressure settings (a value for inspiration pressure and a value for expiration pressure).

Regulation of the device is in this case generally controlled by:
Pressure measurement in the duct, or
Flow measurement in the duct.
This regulation can be applied to:
Turbine rotation speed (as in the case with CPAP ventilators), or
The opening of an optional rate valve which is located on the duct.

The pressure setting is generally set to a value less than 30 mbars, which allows treating pathologies that are a bit more extensive than the CPAP.

The second category is that of expiratory valve respirators.

These devices operate with, on the patient side, a mask without vents and an expiratory valve allowing the gas expired by the patient to be directed out of the device (for example into the surrounding atmosphere), in order to avoid reflux of the gas expired into the duct carrying the gas to the patient.

These respirators are of the barometric or volumetric type.

Barometric respirators are regulated by a pressure setting, the setting can have two different values.

These devices operate therefore according to the repetition of two phases: an inspiratory phase and an expiratory phase. A different value for the pressure setting is assigned to each phase.

These phases are initiated according to pressure or flow measurements.

A flow sensor is integrated into the respirator, in order to follow the volume of gas inhaled by the patient.

The values for pressure settings can be higher than in the case of ventilators for ventilation via leakage: these values can reach about 120 mbar.

Volumetric respirators also operate according to a succession of inspiratory and expiratory phases.

But in this case, a volume of gas defined beforehand must be delivered to the patient by the deliverance of a corresponding flow—the phases are therefore initiated according to the measure of the flow inhaled by the patient, with pressure being a resulting variable and not a controlling variable.

The source of gas is frequently with this type of respirator a bellows or piston apparatus.

It is however also possible for the source of gas to be a turbine. In this case, it is necessary to have fine control of turbine operation.

We have seen above that breathing assistance devices fall into different categories, and that different operating modes are associated with them.

We shall call these different operating modes "respirator modes".

A respirator mode is thus defined by the control variables, controlled variables, but also by the material means implemented (type of duct between the device and the patient, presence or not of an expiratory valve, of pressure sensors in different locations of the device, etc.).

Furthermore, note that there are hybrid devices, providing different operating modes with the same device.

WO 96/11717 demonstrates for example a device in which it is possible to select different respirator modes, using a control panel 320.

The possibility to access different respirator modes with a single device is certainly interesting.

But the device can become complex to handle, because of the different modes that are possible.

In fact, for each respirator mode it can be necessary to adapt the device, by connecting/disconnecting certain parts (such as mentioned above: type of duct, valves, sensors, etc.).

And the known hybrid devices expose patients to incoherencies between a chosen mode and the configuration of the device (in particular concerning parts that are connected to the device).

In fact, the multiplication of respirator modes on the same device also multiplies the risk of manipulation error, since the device can be programmed for a given respirator mode although the correct connections for this mode are not realized.

These incoherencies at best lead to complex implementation (obligation to reconfigure the device), and at worst a danger for the safety of the patient.

BRIEF SUMMARY OF THE TECHNOLOGY

The purpose of the invention is to provide a remedy to these inconveniences.

In order to reach this purpose, the invention offers according to a first aspect a breathing assistance device, capable of operating according to several respiratory modes forming a list of possible modes, and equipped with a means of selecting a desired mode from a group of modes that can be selected, characterized in that the device includes:

means to realize a configuration diagnostic of the device, means to associate a level of authorization with each possible mode, according to the diagnostic results, with the lowest authorization level corresponding to unauthorized modes, means for authorizing only the selection of authorized modes, in such a way that selecting unauthorized modes is impossible.

Preferable but not limited aspects of the method according to the invention are the following:

means to realize a configuration diagnostic of the device are means allowing automatic diagnostic to be realized.

the results of the configuration diagnostic include an indication of a correctly connected expiratory valve, the device includes means for detecting a correctly connected expiratory valve, said means consisting of:
- means to set a pressure setting to be reached at the level of the expiratory valve,
- means of controlling a pressure source for the device to reach this setting at the level of the expiratory valve,
- means to measure a characteristic of said source of pressure when the setting is reached,
- means for deducing from the said characteristic the presence of a correctly connected expiratory valve, said characteristic of the pressure source is energy associated with turbine operation, the results of the configuration diagnostic include an indication that a proximal pressure tap is correctly connected, the authorization levels for modes include:
- a high level corresponding to authorized modes without restriction, and
- an intermediate level corresponding to authorized modes, but associated with a systematic alarm, the device includes means for detecting a change in mode and means for locking the device in case a new mode is detected for which the level of authorization is different from the one of the previously selected mode, the device includes means for detecting a change in mode and means for locking the device in case a new mode is detected corresponding to a change in the authorization level to a lower level, the device includes means for detecting a change in mode and means for locking the device in case a new mode is detected corresponding to a change in the authorization level to a level that is lower than the level of the previously selected mode, the device also includes a means of unlocking that can be accessed according to a particular operating mode, the possible modes include modes destined to be implemented in a "ventilator" configuration of the device, and modes destined to be implemented in a "respirator" configuration of the device, the possible modes include modes destined to be implemented in a "ventilator" configuration of the device, and modes destined to be implemented in a "respirator" configuration of the device, the AIVT mode is selectively associated with a systematic alarm in the case where, during configuration diagnostic, no correct connection of a proximal pressure tap was detected.

According to a second aspect, the invention also offers a method for handling the operation of said device, characterized in that the method includes the following steps:

realization of a configuration diagnostic of the device, association of an authorization level which each possible mode, according to the results of the diagnostic, with the lowest authorization level corresponding to unauthorized modes, selective authorization of authorized modes, in such a way that selecting unauthorized modes is impossible.

A preferable but not limited aspect of the method according to the invention is the following:

mode authorization levels include:
- a high level corresponding to authorized modes without restriction, and
- an intermediate level corresponding to authorized modes, but associated with a systematic alarm.

Other aspects, purposes and advantages of the invention will appear better when the following description of the preferable forms for realizing the invention are read.

DETAILED DESCRIPTION

Figure 1:
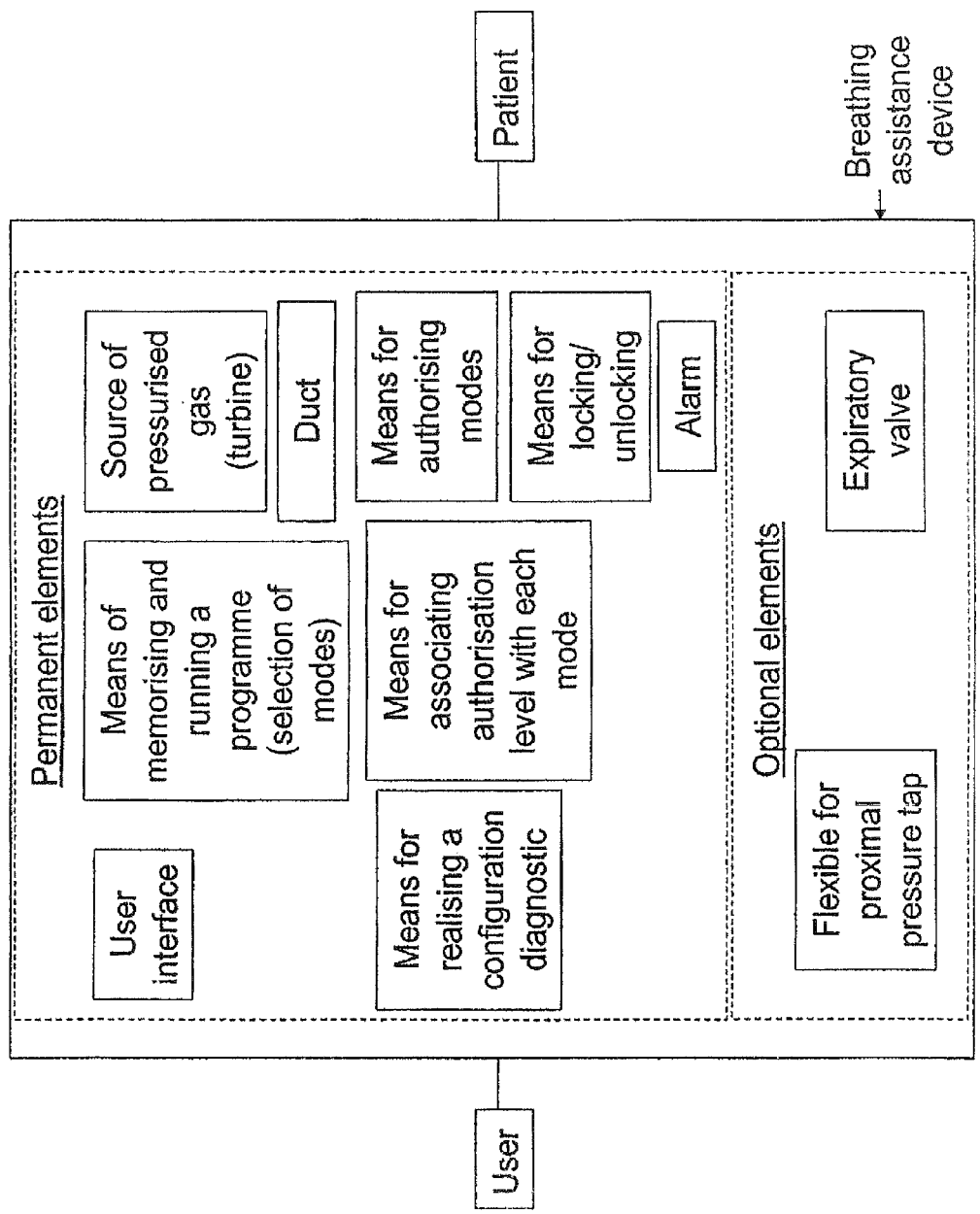
FIG. 1 is a block diagram illustration of a breathing assistance device in accordance with the invention.

General Structure of the Device and Possible Respirator Modes

We shall first describe the means that the device includes according to the invention, as well as the modes associated with a preferable mode for realizing the invention.

This device is in any case a breathing assistance device, capable of operating according to several respiratory modes.

It is a question therefore of a perfected device, of the "hybrid" type.

Possible Respirator Modes:

In a particular embodiment, the device can authorize the following respirator modes:

Modes usually implemented with ventilators. Note that these modes are substantially barometric (since volumetric modes are difficult to implement with ventilators using vented masks, which allow leakage):

S mode (spontaneous):
- This is a mode in which the phases (inspiration and expiration) are triggered solely by the respiratory behavior of the patient,
- One or several sensors (pressure, for example) are usually used to detect the changes in the respiration of the patient, and to consequently trigger the adequate phases,
- It can be said that in this mode the patient "leads", and the device "follows", ST mode (times spontaneous):
- This mode is a variant of the S mode in which a safety triggering of phases is provided if the device does not detect, in the respiratory behavior of the patient and within a given interval of time, the elements that should normally initiate a new phase (such elements will be called "triggering behavior". These triggering behaviors correspond to values of parameters measured by the device—pressure, for example—which are memorized in the device),
- The safety triggering then substitutes itself for the cycle of phases which is normally triggered by the patient, CPAP mode:
- this mode is another variant of the S mode in which the inspiratory pressure and expiratory pressure values are equal, PAC mode (pressure is assisted and controlled):
- in this mode, the device controls triggering of expiratory phases since the duration of the inspiratory phases is set via a parameter in a fixed way in the device,
- as far as the inspiratory phases are concerned, these are triggered by the patient (i.e. when the device has detected a triggering behavior from the patient),
- as with ST mode, a safety triggering of the phases is provided if no triggering behaviour from the patient is detected by the device within a given interval of time, PC mode:
- This mode is a variant of the PAC mode in which not only expiratory phases, but also the inspiratory phases are triggered by the device, Modes that are normally implemented on respirators:

AI mode (aid for inspiration or spontaneous barometric mode):
- This mode corresponds to modes S (and ST if a safety triggering is provided), with an expiratory valve, VPAC mode (ventilation with pressure that is assisted and controlled or controlled barometric mode):
- this mode corresponds to the PAC mode with an expiratory valve,
- phase regulation is ensured using a pressure measurement in the duct: this mode includes a pressure regulation loop, VPC mode:
- This mode corresponds to the PC mode with an expiratory valve, AIVT mode (aid for inspiration with volume ensured):
- This mode can be considered to be barometric as well as volumetric,
- It corresponds to the AI mode, with an extra disposition concerning the volume inhaled by the patient: during inspiratory phases, if the inhaled volume—which is followed by the device—is less than a predetermined value memorized in the device, the device terminates the expiratory phase in "volumetric" mode, forcing a volume of gas to the patient allowing the said predetermined value to be reached for this phase, VAC mode (ventilation assisted and controlled):
- This mode is purely volumetric,
- It corresponds to a declension of the VPAC mode in 100% volumetric: the device operates here with a regulation loop on the flow, VC mode:
- This mode corresponds to a declination of the VPC mode in 100% volumetric.

It thus appears in this preferable mode of realization that many modes are potentially available to the patient.

These potentially available modes will be called "possible" modes.

Note that the above modes correspond only to a preferable example for implementing the invention.

The main principle of the invention can in this way be implemented with a different list of possible modes.

As we shall see, the invention makes it possible to safely and reliably handle such a device that can possible authorize several "possible" modes.

Figure 2:
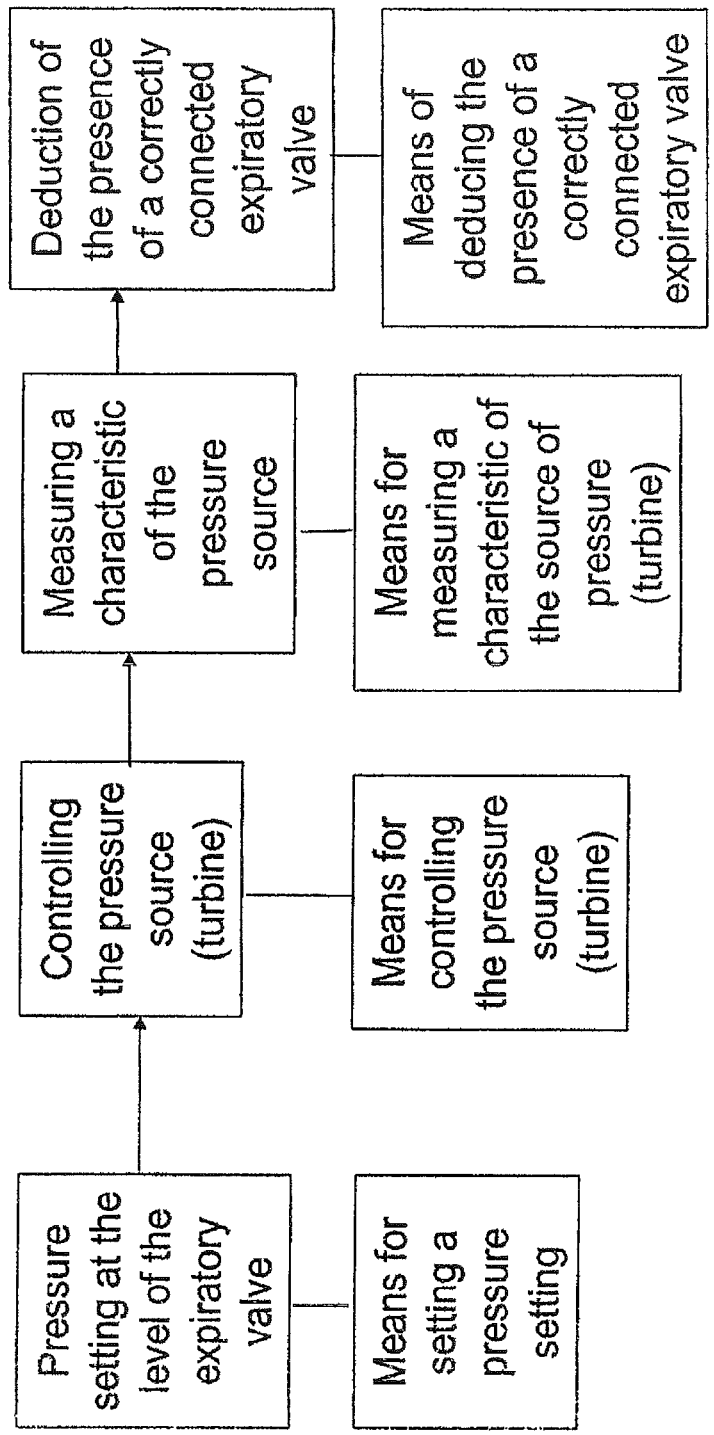
FIG. 2 is a block diagram illustration of a configuration diagnostic step in accordance with one embodiment of the invention.

Structure of the Device—The device itself includes permanent elements, and optional elements that can be associated with the device for certain modes. The general structure of the device is illustrated in FIG. 2.

The permanent elements include in particular:

A source of pressurized gas, for example a turbine capable of being controlled in such a way as to provide a desired pressure or flow, An inspiratory duct (that will simply be called "duct") to carry the gas to the patient, Sensor means to characterize the operation of the device. These means can in particular include:
a sensor of pressure present in the duct,
a sensor of flow passing in this duct, Means for handling the operation of the device. These means can in particular include:
- A user interface to allow the user (patient or doctor, for example):
  - to select a desired mode from the modes offered in a menu. For this purpose the device can include a keyboard, for example,
  - to display the information and data concerning the operation of the device. A display screen, for example, can be provided for this purpose,
- means of memorizing and running a program allowing a selected mode to be implemented.
  - These means thus allow in particular to trigger the inspiratory and expiratory phases (according to the triggering behavior detected with the patient using sensor means, or according to predetermined parameters memorized in the device),
- means allowing to realize a configuration diagnostic of the device.
  - We will discuss the role of these means,
- means for associating a level of authorization with each possible mode, according to the results of the diagnostic, with the lowest level of authorization corresponding to unauthorized modes,
- means for authorizing at the level of the user interface only the selection of authorized modes, in such a way that the selection of unauthorized modes is impossible.

The device also includes connectors that make it possible to connect:
- a flexible with pneumatic control of an expiratory valve, in order to allow such a valve to be opened and closed when it is connected to the device,
- a proximal pressure tap for the connection of a flexible of which the other end is connected to the mask of the patient, allowing pressure at the level of the patient to be determined (this pressure is called "proximal pressure").

The optional elements of the device include thus in particular the expiratory valve and the flexible for proximal pressure tap.

These optional elements can be connected to the device or not, according to the mode selected.

Operation of the Device—The device according to the invention is thus a device capable of operating according to several possible modes.

Each one of these modes can require the presence of specific optional elements.

And on the contrary, it can be desired to avoid connecting certain optional elements for certain modes.

Connecting the different optional elements to the device defines a "configuration" of the device. And the device can therefore be configured in different way, according to the optional elements that are connected.

Configuration diagnostic—The invention implements a step of configuration diagnostic of the device, in order to establish a list of the optional elements that are effectively connected to the device.
Concerning the frequency of realizing such a diagnostic:
This step of the diagnostic can be implemented each time the device is turned on,
It can also be implemented every time a new mode is selected,
And it can also be implemented periodically in a systematic way, for the purpose of verifying the proper configuration of the device,
Note that the above-mentioned solutions can be combined.

This diagnostic step can be realized automatically, via means of automatic diagnostic of the device.

In this case, said means of automatic diagnostic are programmed to perform the configuration diagnostic when this is desired (see the different possibilities for frequency for realizing the above diagnostic).

Such automatic means of diagnostic allow the optional elements that are connected to the device to be determined automatically.

In the case described here the optional elements include the expiratory valve and the flexible proximal pressure tap.

In order to detect the proper connection of an expiratory valve, these automatic diagnostic means can perform the following operations, also illustrated in FIG. 2:
setting the pressure setting to be reached at the level of the expiratory valve,
controlling the pressure source of the device (the turbine in the case described here) to reach this setting at the level of the expiratory valve,
Note to this effect that the expiratory valve is controlled pneumatically par the control flexible mentioned above, since this flexible is fed by the pressure source for the device,
measure a characteristic of said source of pressure when the setting is reached,
This characteristic can for example be the energy absorbed by the turbine in order to provide pressure in the duct, allowing the pressure setting to be reached at the level of the expiratory valve,
deduction, according to the said characteristic, of the presence of a correctly connected expiratory valve,
if the turbine has only absorbed a small amount of energy in order to allow reaching the pressure setting at the level of the expiratory valve, this means that the expiratory valve is correctly connected. If the absorbed energy is high, the connection is not realized, or it is defective.
In this case two ranges of values for energy absorbed by the turbine are predefined and memorized in the device in order to determine respectively a range corresponding to a valve that is correctly connected, and a range corresponding to a valve that is incorrectly connected.

The automatic means of diagnostic include therefore in this case means that allow these different operations to be performed. Such means are connected to the memory and to the programmed mentioned above.

In order to detect proper connection of a flexible for proximal pressure tap, the automatic means of diagnostic include:
A pressure sensor at the level of the connection for the flexible for proximal pressure tap,
This sensor indicates the proximal pressure when the flexible is connected,
This proximal pressure corresponds, when the flexible is connected, to the pressure at the level of the duct, taking a load loss into account (which is according to, among other things, the length of the duct between the duct pressure tap and the proximal pressure tap),
In the absence of a flexible, the proximal pressure sensor indicates low pressure,
Means of comparing the values of the pressure at the level of the duct and the proximal pressure,
Means allowing to establish according to this comparison if a flexible for proximal pressure tap is correctly connected to the device. If the difference between the two measured pressures exceeds a predetermined threshold memorized in the device, the automatic means of diagnostic therefore indicate that the flexible for proximal pressure tap is not connected.

Note that in a simplified variant for implementing the invention, the diagnostic can be realized by the user himself, using instructions provided by the device.

In this variant, the means of the device making it possible to realize a diagnostic is a "check-list" of connections to be checked which is displayed on the screen when the diagnostic is required (see above for the different possibilities of frequency for implementing the diagnostic).

In all cases, this step of configuration diagnostic for the device makes it possible to establish the list of optional elements that are effectively connected to the device.

Assigning authorization levels to the modes Different authorization levels are memorized in the device.

There can be any number of levels. It must greater than or equal to two, with the lowest level corresponding as we shall see to an "unauthorized" level.

And at the end of the configuration diagnostic step, the device will automatically associate one of these authorization levels to each of the possible modes for the device.

In this example, three authorization levels are defined:
Level 0: unauthorized mode,
Level 1: authorized mode, but associated with a systematic alarm. This is an intermediate level,
Level 2: authorized mode, without systematic alarm and without restriction.

Associating a level to each mode takes place according to a given law of transfer:
  for which one input is the list of optional elements that were detected as being correctly connected during the diagnostic step,
  and for which the output is the list of pairs (mode, associated authorization level).

To implement this association of an authorization level with each mode, the device uses a means of calculation implementing a processor, which is connected to the memory of the device.

The transfer matrix, which corresponds to the transfer function, is also memorized in this memory.

In the example described here, this matrix is as follows:

| Mode assignment coefficient | | Mode | | | | | | | | | |
|---|---|---|---|---|---|---|---|---|---|---|---|
| | | S | ST | CPAP | PAC | PC | AI | VPAC | VPC | AIVT | VAC | VC |
| Optional Element | Expiratory | 0 | 0 | 0 | 0 | 0 | 2 | 2 | 2 | 2 | 2 | 2 |
| | Valve | 2 | 2 | 2 | 2 | 2 | 0 | 0 | 0 | 0 | 0 | 0 |
| | Proximal | 1 | 1 | 1 | 1 | 1 | 1 | 1 | 1 | 1 | 1 | 1 |
| | pressure | 1 | 1 | 1 | 1 | 1 | 1 | 1 | 1 | 0.5 | 1 | 1 |

This matrix includes for each mode (each column) four mode assignment codes.

Two coefficients are associated with each optional element:
  a coefficient that is assigned to the mode if correct connection of the element was detected during diagnostic (top line in the cell),
  a coefficient which is assigned to the mode if correct connection of the element was not detected during diagnostic (bottom line in the cell).

A coefficient per optional element is thus associated with each mode (here then two coefficients are associated to each mode).

The level associated with each mode is then obtained by multiplying the coefficients associated to the mode amongst themselves.

Note that this mode of "calculation" of the level associated with each mode can be different, and any law of correspondence between the detected optional elements and the assigned levels can be defined and memorized in the device.

In the case shown here, we see that:
  modes S, ST, CPAP, PAC, PC will be assigned the level 0 (unauthorized modes) if the expiratory valve is connected,
  modes AI, VPAC, VPC, AIVT, VAC, VC will be assigned, on the contrary, level 0 if the expiratory valve is not connected,
  in the case where the expiratory valve is connected, the AIVT mode will be assigned an intermediate level (1 instead of 2) if the proximal pressure tap is not connected.

Selective authorization of modes—Once the assigning of an authorization level for each mode has been performed, the device has in memory the correspondence between the modes and their associated level.

This correspondence is going to be determinant for handling the operation of the device.

In fact, the device includes means for updating the menu of modes offered to the user, according to the authorization levels of the modes.

In this way, a mode that is associated with level 0 will not be able to be selected by the user.

The device can for example to this effect automatically delete the unauthorized modes from the menu of modes offered for selection, or selectively deactivate the selection keys for these unauthorized modes, in the case where selection is made by pressing a key that is dedicated to that mode.

And the modes that are associated to level 1 (which can be the case here with AIVT mode) can of course be selected by the user, but their implementation is associated with a systematic alarm that signals that an optional element that is normally connected for this mode is not connected.

This alarm can ring only when the mode is selected, or be maintained during the entire implementation of the mode.

It can be replaced with an alert message for the user.

Locking the device—We have seen above that according to the authorization level assigned to each mode, the mode can be offered for selection or be removed from selection.

We have also seen that intermediate authorization levels can allow a mode to be selected, with certain restrictions (systematic alarm).

We have also seen that the process mentioned above, that begins with a configuration diagnostic and that ends with the associations of levels with modes, can be initialized at different occasions, and according to different methods.

We shall describe below a variant in which means for locking the device are provided in the case of incorrect use of the device.

When a new association of levels has been performed and the device is in service (a mode has been selected), the device can include means to check that the mode that is selected is correctly associated with the level which allows this selection.

In this variant the device includes means of detecting that the mode has been changed and means for locking the device in case a new mode is detected for which the authorization level is different from that of the previously selected mode.

It is possible to implement such a locking only if the new detected mode is associated with a level that is lower than the previously selected mode.

It is also possible to implement this locking only if the level associated with the newly-selected mode is the lowest level ("unauthorized" level).

Locking the device can lead to a blocking of its functions, and/or an alarm, and/or automatic shut off after a lapse of time and a warning.

And it is also possible to allow a particular user to unlock the device, according to a particular operating mode that he is aware of.

This particular operating mode can be the key entry of a code using the device's keyboard, or a specific sequence for manipulating the keys of the device.

It thus appears that the invention makes it possible to efficiently, safely and reliably handle, the operation of a device likely to propose several modes.

Indeed, the selective authorization of different modes as a function of the configuration of the device (i.e. as a function of the optional elements effectively connected to the device) allows great flexibility, while at the same time great security of the operation of the device.

It should be noted that some devices have proposed some forms of differentiated operating levels.

WO 97/06844 discloses an example of such device.

The device of this document can operate according to a "basic mode", or according to an "advanced mode".

But in this case, the selective authorizations are not derived from a configuration step.

Thus, the perspective of the device of WO 97/06844 is quite different from the present invention.

Furthermore, the device of WO 97/06844 is not even designed to operate with different configurations.

WO 00/51663 teaches another example of device which implies some form of different operating levels.

But here again, the different levels are not authorized as a function of any "configuration" whatsoever (i.e. as a function of optional elements which would be connected on the device).

In this device indeed, the selective authorizations are open as a function of the identity of the operator, and of his skills.

Furthermore, in any case the "authorization levels" of this last known device do not correspond to different modes—they rather correspond to a selective access to different physical resources of the device (drugs, components, . . . ).

And here again, the device is not designed to operate with different configurations.

It thus appear that the device according to the invention provides an original and efficient solution for operating a single device in different modes and with different optional elements (such as a vented mask, or an expiratory valve . . . ) connected to it, the associated flexibility being nevertheless associated with a maximum degree of security.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A respiratory treatment apparatus comprising:
   a controllable source of breathable gas;
   an inspiratory duct coupled to the controllable source of breathable gas and adapted to carry the breathable gas away from the controllable source to a patient;
   a sensor configured to detect a characteristic of the operation of the apparatus;
   and
   a controller coupled with the source of breathable gas, the controller being configured to determine a relation of the characteristic compared to a predetermined threshold, and to operate the source of breathable gas in a plurality of respiratory treatment modes of operation, including a first respirator mode and a second ventilator mode, wherein the controller being further configured to authorize at least one of the plurality of respiratory treatment modes of operation based on the determined relation of the characteristic.

2. The apparatus of claim 1 wherein the controller is configured to control a user interface to prevent user selection of at least one of the respiratory treatment modes of operation based on the determined relation of the characteristic.

3. The apparatus of claim 1 wherein one of the plurality of respiratory treatment modes of operation is a spontaneous mode.

4. The apparatus of claim 1 wherein one of the plurality of respiratory treatment modes of operation is a vpac mode.

5. The apparatus of claim 1 wherein the controller is configured to detect the presence of at least one of first and second optional ventilation components based on the determined relation of the characteristic, wherein the first component comprises an expiratory valve.

6. The apparatus of claim 5 wherein the second component comprises a pressure tap.

7. The apparatus of claim 1 wherein the controller controls a pressure setting of the controllable source of breathable gas.

8. The apparatus of claim 7 wherein the controllable source of breathable gas comprises a turbine.

9. The apparatus of claim 1 wherein the controller is configured to determine a relation of the characteristic compared to the predetermined threshold each time a new mode of operation of the plurality of respiratory treatment modes of operation is selected with a user interface of the apparatus.

10. The apparatus of claim 1 wherein the controller is configured to determine a relation of the characteristic compared to the predetermined threshold each time operation of the apparatus is initiated.

11. The apparatus according to claim 1, wherein the characteristic of the operation of the apparatus is the energy absorbed by the controllable source of breathable gas required to provide the detected pressure, wherein the energy absorbed is compared to a predefined range of energy absorbed values to determine the authorized at least one modes of operation.

12. The apparatus according to claim 1, wherein the sensor is a pressure sensor, and the characteristic of the operation of the apparatus is a difference in pressure between an end of the duct closer to the patient and an end of the duct closer to the controllable source, wherein the difference in pressure is compared to the predetermined threshold to determine the authorized at least one modes of operation.

13. A respiratory treatment apparatus comprising:
   a controllable supply means for supplying breathable gas to a user of the respiratory treatment apparatus through a duct coupled to the controllable supply means;
   a sensing means for detecting a characteristic of the operation of the apparatus;
   a diagnostic means for determining a relation of the characteristic detected by the sensing means as compared to a predetermined threshold; and
   a processing means coupled with the supply means, the processing means for operating the supply means in a plurality of respiratory treatment modes of operation including a first mode that is normally implemented by a respirator and a second mode that is normally implemented by a ventilator, and for authorizing at least one of the plurality of respiratory treatment modes of operation based on the determination of the diagnostic means.

14. The apparatus of claim 13 wherein the processing means is configured to control a user interface to prevent user selection of at least one of the respiratory treatment modes of operation based on the determination of the diagnostic means.

15. The apparatus of claim 13 wherein one of the plurality of respiratory treatment modes of operation is a spontaneous mode.

16. The apparatus of claim 13 wherein one of the plurality of respiratory treatment modes of operation is a vpac mode.

17. The apparatus of claim 13 wherein the diagnostic means is capable of detecting the presence of at least one of first and second optional ventilation components based on the determination of the diagnostic means, wherein the first component comprises an expiratory valve.

18. The apparatus of claim 15 wherein the second component comprises a pressure tap.

19. The apparatus of claim 13 wherein the processing means controls a pressure setting of the controllable supply means.

20. The apparatus of claim 13 wherein the processing means initiates the diagnostic means each time a new mode of operation of the plurality of respiratory treatment modes of operation is selected with a user interface of the apparatus.

21. The apparatus of claim 13 wherein the processing means initiates the diagnostic means each time operation of the apparatus is initiated.

22. The apparatus according to claim 13, wherein the characteristic of the operation of the apparatus is the energy absorbed by the controllable source of breathable gas required to provide the detected pressure, wherein the energy absorbed is compared to a predefined range of energy absorbed values to determine the authorized at least one modes of operation.

23. The apparatus according to claim 13, wherein the sensing means is a pressure sensing means for detecting a difference in pressure between an end of the duct closer to the patient and an end of the duct closer to the controllable supply means, the difference in pressure being compared to the predetermined threshold to determine the authorized at least one modes of operation.

* * * * *